US010944290B2

(12) United States Patent
Mirjalili et al.

(10) Patent No.: US 10,944,290 B2
(45) Date of Patent: Mar. 9, 2021

(54) HEADGEAR PROVIDING INDUCTIVE COUPLING TO A CONTACT LENS

(71) Applicant: Tectus Corporation, Saratoga, CA (US)

(72) Inventors: Ramin Mirjalili, San Jose, CA (US); Hawk Yin Pang, San Jose, CA (US); Richard Gioscia, New Jersey, CA (US); Michael West Wiemer, San Jose, CA (US)

(73) Assignee: Tectus Corporation, Saratoga, CA (US)

( * ) Notice: Subject to any disclaimer, the term of this patent is extended or adjusted under 35 U.S.C. 154(b) by 0 days.

(21) Appl. No.: 16/530,949

(22) Filed: Aug. 2, 2019

(65) Prior Publication Data

US 2021/0036549 A1   Feb. 4, 2021

(51) Int. Cl.
*G02C 7/04*   (2006.01)
*H02J 50/10*   (2016.01)
(Continued)

(52) U.S. Cl.
CPC ............... *H02J 50/10* (2016.02); *G02C 7/04* (2013.01); *G02C 11/10* (2013.01); *H01F 38/14* (2013.01); *H02J 50/70* (2016.02); *H04R 1/028* (2013.01)

(58) Field of Classification Search
CPC .......... G02C 7/04; A61B 5/6814; H02J 50/10; H02J 7/025; G02B 27/017
(Continued)

(56) References Cited

U.S. PATENT DOCUMENTS

| 4,014,321 A | 3/1977 | March |
| 4,577,545 A | 3/1986 | Kemeny |

(Continued)

FOREIGN PATENT DOCUMENTS

| CA | 2280022 | 1/2001 |
| CA | 2280022 A1 | 1/2001 |

(Continued)

OTHER PUBLICATIONS

Avestruz, A-T. et al., "Single-Sided AC Magnetic Fields for Induction Heating," 39th Annual Conference of the IEEE, Nov. 10-13, 2013, pp. 5052-5057.

(Continued)

*Primary Examiner* — Rexford N Barnie
*Assistant Examiner* — Thai H Tran
(74) *Attorney, Agent, or Firm* — Fenwick & West LLP

(57) ABSTRACT

A transmitter coil inductively couples to a receiver coil contained in a contact lens. In one approach, the transmitter coil is contained in a headgear, for example a head band. When the user wears the headgear, the transmitter coil is positioned on a side of the user's head and between the user's ear and the user's eye opening. In one implementation, a head band loops from one ear behind the user's head to the other ear, and also extends slightly forward of each ear. The transmitter coil(s) may be located in the portion of the headband that extends forward of each ear. This places the transmitter coil close to the receiver coil, typically within 40-50 mm of the user's eye opening, while still maintaining an unobtrusive aesthetic.

18 Claims, 11 Drawing Sheets
(2 of 11 Drawing Sheet(s) Filed in Color)

(51) Int. Cl.
*H01F 38/14* (2006.01)
*H04R 1/02* (2006.01)
*G02C 11/00* (2006.01)
*H02J 50/70* (2016.01)
*A61B 5/00* (2006.01)
*G02B 27/01* (2006.01)
*H02J 7/02* (2016.01)

(58) Field of Classification Search
USPC .......................................... 307/104; 320/108
See application file for complete search history.

(56) References Cited

U.S. PATENT DOCUMENTS

| | | | |
|---|---|---|---|
| 4,871,247 A | 10/1989 | Haynes | |
| 4,941,068 A | 7/1990 | Hofmann | |
| 5,331,149 A | 7/1994 | Spitzer | |
| 5,467,104 A | 11/1995 | Furness, III | |
| 5,638,218 A | 6/1997 | Oomura | |
| 5,638,219 A | 6/1997 | Medina Puerta | |
| 5,682,210 A | 10/1997 | Weirich | |
| 5,699,193 A | 12/1997 | Monno | |
| 5,712,721 A | 1/1998 | Large | |
| 5,726,916 A | 3/1998 | Smyth | |
| 6,120,460 A | 9/2000 | Abreu | |
| 6,181,287 B1 | 1/2001 | Beigel | |
| 6,215,593 B1 | 4/2001 | Bruce | |
| 6,307,945 B1 | 10/2001 | Hall | |
| 6,312,393 B1 | 11/2001 | Abreu | |
| 6,509,743 B1 | 1/2003 | Ferrero | |
| 6,570,386 B2 | 5/2003 | Goldstein | |
| 6,594,370 B1 | 7/2003 | Anderson | |
| 6,823,171 B1 | 11/2004 | Kaario | |
| 6,851,805 B2 | 2/2005 | Blum | |
| 6,920,283 B2 | 7/2005 | Goldstein | |
| 7,088,235 B1 | 8/2006 | Carricut | |
| 7,137,952 B2 | 11/2006 | Leonardi | |
| 7,359,059 B2 | 4/2008 | Lust | |
| 7,562,445 B2 | 7/2009 | Lerch | |
| 7,626,562 B2 | 12/2009 | Iwasaki | |
| 7,758,187 B2 | 7/2010 | Amirparviz | |
| 7,835,056 B2 | 11/2010 | Doucet | |
| 7,893,832 B2 | 2/2011 | Laackmann | |
| 7,931,832 B2 | 4/2011 | Pugh | |
| 8,077,245 B2 | 12/2011 | Adamo | |
| 8,087,777 B2 | 1/2012 | Rosenthal | |
| 8,096,654 B2 | 1/2012 | Amirparviz | |
| 8,348,422 B2 | 1/2013 | Pugh | |
| 8,348,424 B2 | 1/2013 | Pugh | |
| 8,394,660 B2 | 3/2013 | Kim | |
| 8,398,239 B2 | 3/2013 | Horning | |
| 8,430,310 B1 | 4/2013 | Ho | |
| 8,441,731 B2 | 5/2013 | Sprague | |
| 8,446,341 B2 | 5/2013 | Amirparviz | |
| 8,482,858 B2 | 7/2013 | Sprague | |
| 8,520,309 B2 | 8/2013 | Sprague | |
| 8,526,879 B2 | 9/2013 | Kristiansen | |
| 8,579,434 B2 | 11/2013 | Amirparviz | |
| 8,582,209 B1 | 11/2013 | Amirparviz | |
| 8,608,310 B2 | 12/2013 | Otis | |
| 8,632,182 B2 | 1/2014 | Chen | |
| 8,721,074 B2 | 5/2014 | Pugh | |
| 8,764,185 B1 | 7/2014 | Biederman | |
| 8,781,570 B2 | 7/2014 | Chuang | |
| 8,786,520 B2 | 7/2014 | Legerton | |
| 8,786,675 B2 | 7/2014 | Deering | |
| 8,798,332 B2 | 8/2014 | Otis | |
| 8,827,445 B1 | 9/2014 | Wiser | |
| 8,830,571 B1 | 9/2014 | Vizgaitis | |
| 8,870,370 B1 | 10/2014 | Otis | |
| 8,874,182 B2 | 10/2014 | Etzkorn | |
| 8,906,088 B2 | 12/2014 | Pugh | |
| 8,911,078 B2 | 12/2014 | Meyers | |
| 8,922,898 B2 | 12/2014 | Legerton | |
| 8,926,809 B2 | 1/2015 | Pletcher | |
| 8,931,906 B2 | 1/2015 | Huang | |
| 8,960,898 B1 | 2/2015 | Etzkorn | |
| 8,963,268 B2 | 2/2015 | Kim | |
| 8,964,298 B2 | 2/2015 | Haddick | |
| 8,971,978 B2 | 3/2015 | Ho | |
| 8,985,763 B1 | 3/2015 | Etzkorn | |
| 8,989,834 B2 | 3/2015 | Ho | |
| 9,000,000 B2 | 4/2015 | Carroll | |
| 9,028,068 B2 | 5/2015 | Chang | |
| 9,039,171 B2 | 5/2015 | Groisman | |
| 9,040,923 B2 | 5/2015 | Sprague | |
| 9,047,512 B2 | 6/2015 | Otis | |
| 9,048,389 B2 | 6/2015 | Fu | |
| 9,052,528 B2 | 6/2015 | Pugh | |
| 9,052,533 B2 | 6/2015 | Pugh | |
| 9,054,079 B2 | 6/2015 | Etzkorn | |
| 9,058,053 B2 | 6/2015 | Covington | |
| 9,063,351 B1 | 6/2015 | Ho | |
| 9,063,352 B2 | 6/2015 | Ford | |
| 9,111,473 B1 | 8/2015 | Ho | |
| 9,130,099 B2 | 9/2015 | Robin | |
| 9,130,122 B2 | 9/2015 | Fu | |
| 9,134,546 B2 | 9/2015 | Pugh | |
| 9,153,074 B2 | 10/2015 | Zhou | |
| 9,158,133 B1 | 10/2015 | Pletcher | |
| 9,161,712 B2 | 10/2015 | Etzkorn | |
| 9,170,646 B2 | 10/2015 | Toner | |
| 9,178,107 B2 | 11/2015 | Tsai | |
| 9,192,298 B2 | 11/2015 | Bouwstra | |
| 9,195,075 B2 | 11/2015 | Pugh | |
| 9,196,094 B2 | 11/2015 | Ur | |
| 9,215,293 B2 | 12/2015 | Miller | |
| 9,217,881 B2 | 12/2015 | Pugh | |
| 9,225,375 B2 | 12/2015 | Pugh | |
| 9,244,285 B2 | 1/2016 | Chen | |
| 9,271,677 B2 | 3/2016 | Leonardi | |
| 9,282,920 B2 | 3/2016 | Ho | |
| 9,289,123 B2 | 3/2016 | Weibel | |
| 9,289,954 B2 | 3/2016 | Linhardt | |
| 9,298,002 B2 | 3/2016 | Border | |
| 9,298,020 B1 | 3/2016 | Etzkorn | |
| D754,861 S | 4/2016 | Etzkorn | |
| 9,307,905 B2 | 4/2016 | Varel | |
| 9,310,626 B2 | 4/2016 | Pugh | |
| 9,316,848 B2 | 4/2016 | Pugh | |
| 9,326,710 B1 | 5/2016 | Liu | |
| 9,332,935 B2 | 5/2016 | Etzkorn | |
| 9,335,562 B2 | 5/2016 | Pugh | |
| 9,341,843 B2 | 5/2016 | Border | |
| 9,366,872 B2 | 6/2016 | Honea | |
| 9,366,881 B2 | 6/2016 | Pugh | |
| 9,389,433 B2 | 7/2016 | Pugh | |
| 9,401,454 B2 | 7/2016 | Robin | |
| 9,414,746 B2 | 8/2016 | Bergman | |
| 9,425,359 B2 | 8/2016 | Tsai | |
| 9,442,307 B2 | 9/2016 | Meyers | |
| 9,442,310 B2 | 9/2016 | Biederman | |
| 9,445,768 B2 | 9/2016 | Alexander | |
| 9,523,865 B2 | 12/2016 | Pletcher | |
| 9,629,774 B2 | 4/2017 | Dayal | |
| 9,728,981 B2 | 8/2017 | Lee | |
| 9,810,926 B2 | 11/2017 | Sako | |
| 9,939,658 B1 | 4/2018 | Gutierrez | |
| 10,025,118 B1 | 7/2018 | Markus | |
| 10,117,740 B1* | 11/2018 | Lee | G02C 7/04 |
| 10,278,644 B1 | 5/2019 | Etzkorn | |
| 2002/0084904 A1 | 7/2002 | De La Huerga | |
| 2002/0101383 A1 | 8/2002 | Junod | |
| 2003/0158588 A1* | 8/2003 | Rizzo | A61N 1/0543 607/54 |
| 2003/0171792 A1* | 9/2003 | Zarinetchi | A61N 1/378 607/61 |
| 2003/0173408 A1 | 9/2003 | Mosher | |
| 2003/0179094 A1 | 9/2003 | Abreu | |
| 2004/0027536 A1 | 2/2004 | Blum | |
| 2005/0075693 A1* | 4/2005 | Toy | A61N 1/37223 607/60 |
| 2005/0159791 A1* | 7/2005 | Daly | H04R 25/606 607/57 |

(56) References Cited

U.S. PATENT DOCUMENTS

| | | |
|---|---|---|
| 2005/0179604 A1 | 8/2005 | Liu |
| 2006/0177086 A1 | 8/2006 | Rye |
| 2006/0290882 A1 | 12/2006 | Meyers |
| 2007/0024423 A1 | 2/2007 | Nikitin |
| 2007/0157828 A1* | 7/2007 | Susel ............... H01F 41/076 101/35 |
| 2007/0241986 A1 | 10/2007 | Lee |
| 2008/0165072 A1 | 7/2008 | Schlager |
| 2009/0058189 A1 | 3/2009 | Cook |
| 2009/0066722 A1 | 3/2009 | Kriger |
| 2009/0072628 A1 | 3/2009 | Cook |
| 2009/0243397 A1* | 10/2009 | Cook ............... H02J 50/12 307/104 |
| 2009/0244477 A1 | 10/2009 | Pugh |
| 2010/0001926 A1 | 1/2010 | Amirparviz |
| 2010/0110372 A1 | 5/2010 | Pugh |
| 2010/0136905 A1 | 6/2010 | Kristiansen |
| 2010/0234717 A1 | 9/2010 | Wismer |
| 2010/0253476 A1 | 10/2010 | Poutiatine |
| 2010/0308749 A1 | 12/2010 | Liu |
| 2011/0034134 A1 | 2/2011 | Henderson |
| 2011/0221659 A1 | 9/2011 | King, III |
| 2012/0105226 A1 | 5/2012 | Bourdeau |
| 2012/0262003 A1 | 10/2012 | Tetu |
| 2013/0050432 A1 | 2/2013 | Perez |
| 2013/0093254 A1* | 4/2013 | Urano ............... H02J 7/0029 307/104 |
| 2013/0100139 A1 | 4/2013 | Schliesser |
| 2013/0242077 A1 | 9/2013 | Lin |
| 2013/0270664 A1 | 10/2013 | Kim |
| 2014/0016097 A1 | 1/2014 | Leonardi |
| 2014/0063054 A1 | 3/2014 | Osterhout |
| 2014/0081178 A1 | 3/2014 | Pletcher |
| 2014/0098226 A1 | 4/2014 | Pletcher |
| 2014/0120983 A1 | 5/2014 | Lam |
| 2014/0192311 A1 | 7/2014 | Pletcher |
| 2014/0198186 A1 | 7/2014 | Hong |
| 2014/0200424 A1* | 7/2014 | Etzkorn ............... A61B 5/6821 600/345 |
| 2014/0240665 A1 | 8/2014 | Pugh |
| 2014/0252868 A1 | 9/2014 | Yamada |
| 2014/0292620 A1 | 10/2014 | Lapstun |
| 2014/0371560 A1 | 12/2014 | Etzkorn |
| 2015/0005604 A1 | 1/2015 | Biederman |
| 2015/0016777 A1 | 1/2015 | Abovitz |
| 2015/0060904 A1 | 3/2015 | Robin |
| 2015/0062533 A1 | 3/2015 | Toner |
| 2015/0072615 A1 | 3/2015 | Mofidi |
| 2015/0088253 A1 | 3/2015 | Doll |
| 2015/0123785 A1 | 5/2015 | Haflinger |
| 2015/0126845 A1 | 5/2015 | Jin |
| 2015/0145095 A1 | 5/2015 | Kim |
| 2015/0147975 A1 | 5/2015 | Li |
| 2015/0148628 A1 | 5/2015 | Abreu |
| 2015/0150510 A1 | 6/2015 | Leonardi |
| 2015/0171274 A1 | 6/2015 | Guo |
| 2015/0173602 A1 | 6/2015 | Barrows |
| 2015/0223684 A1 | 8/2015 | Hinton |
| 2015/0227735 A1 | 8/2015 | Chappell |
| 2015/0234205 A1 | 8/2015 | Schowengerdt |
| 2015/0235439 A1 | 8/2015 | Schowengerdt |
| 2015/0235440 A1 | 8/2015 | Schowengerdt |
| 2015/0235444 A1 | 8/2015 | Schowengerdt |
| 2015/0235446 A1 | 8/2015 | Schowengerdt |
| 2015/0235457 A1 | 8/2015 | Schowengerdt |
| 2015/0235468 A1 | 8/2015 | Schowengerdt |
| 2015/0235471 A1 | 8/2015 | Schowengerdt |
| 2015/0241698 A1 | 8/2015 | Schowengerdt |
| 2015/0243090 A1 | 8/2015 | Schowengerdt |
| 2015/0261294 A1 | 9/2015 | Urbach |
| 2015/0281411 A1 | 10/2015 | Markus |
| 2015/0301338 A1 | 10/2015 | Van Heugten |
| 2015/0305929 A1 | 10/2015 | Goldberg |
| 2015/0339857 A1 | 11/2015 | O'Connor |
| 2015/0362750 A1 | 12/2015 | Yeager |
| 2015/0362752 A1 | 12/2015 | Linhardt |
| 2015/0372395 A1 | 12/2015 | Lavedas |
| 2015/0380461 A1 | 12/2015 | Robin |
| 2015/0380988 A1 | 12/2015 | Chappell |
| 2016/0006115 A1 | 1/2016 | Etzkorn |
| 2016/0011419 A1 | 1/2016 | Gao |
| 2016/0018650 A1 | 1/2016 | Haddick |
| 2016/0018651 A1 | 1/2016 | Haddick |
| 2016/0018652 A1 | 1/2016 | Haddick |
| 2016/0018653 A1 | 1/2016 | Haddick |
| 2016/0030160 A1 | 2/2016 | Markus |
| 2016/0049544 A1 | 2/2016 | Robin |
| 2016/0066825 A1 | 3/2016 | Barrows |
| 2016/0080855 A1 | 3/2016 | Greenberg |
| 2016/0091737 A1 | 3/2016 | Kim |
| 2016/0093666 A1 | 3/2016 | Gilet |
| 2016/0097940 A1 | 4/2016 | Sako |
| 2016/0113760 A1 | 4/2016 | Conrad |
| 2016/0141449 A1 | 5/2016 | Robin |
| 2016/0141469 A1 | 5/2016 | Robin |
| 2016/0143728 A1 | 5/2016 | De Smet |
| 2016/0147301 A1 | 5/2016 | Iwasaki |
| 2016/0154256 A1 | 6/2016 | Yajima |
| 2016/0172536 A1 | 6/2016 | Tsai |
| 2016/0172869 A1 | 6/2016 | Park |
| 2016/0204307 A1 | 7/2016 | Robin |
| 2016/0223842 A1 | 8/2016 | Yun |
| 2016/0253831 A1 | 9/2016 | Schwarz |
| 2016/0261142 A1 | 9/2016 | Park |
| 2016/0270176 A1 | 9/2016 | Robin |
| 2016/0270187 A1 | 9/2016 | Robin |
| 2016/0276328 A1 | 9/2016 | Robin |
| 2016/0299354 A1 | 10/2016 | Shtukater |
| 2017/0023793 A1 | 1/2017 | Shtukater |
| 2017/0042480 A1 | 2/2017 | Gandhi |
| 2017/0168322 A1 | 6/2017 | Toner |
| 2017/0188848 A1 | 7/2017 | Banet |
| 2017/0189699 A1 | 7/2017 | Dellamano |
| 2017/0231337 A1 | 8/2017 | Anderson |
| 2017/0234818 A1 | 8/2017 | Jesme |
| 2017/0255026 A1 | 9/2017 | Rakhyani |
| 2017/0270636 A1 | 9/2017 | Shtukater |
| 2017/0319099 A1* | 11/2017 | Levinson ............... A61B 5/6803 |
| 2017/0337461 A1 | 11/2017 | Jesme |
| 2017/0371184 A1 | 12/2017 | Shtukater |
| 2018/0036974 A1 | 2/2018 | Hahn |
| 2018/0212313 A1 | 7/2018 | Harper |
| 2019/0074823 A1 | 3/2019 | Der |

FOREIGN PATENT DOCUMENTS

| | | |
|---|---|---|
| WO | 2016014118 A1 | 1/2016 |
| WO | 2016022665 A1 | 2/2016 |
| WO | 2016150630 A1 | 9/2016 |
| WO | 2016195201 A1 | 12/2016 |
| WO | 2019069555 | 7/2018 |

OTHER PUBLICATIONS

Chronos Vision GmbH, "Scleral Search Coils 2D/3D," 4 pages, [Online][Retrieved Feb. 28, 2019], Retrieved from the internet <http://www.chronos-vision.de/downloads/CV Product SSC.pdf>. (4 pages).

Kao, H-L. et al., "DuoSkin: Rapidly Prototyping On-Skin User Interfaces Using Skin-Friendly Materials," ISWC '16, ACM, Sep. 12-16, 2016, 8 pages.

Kenyon, R.V., "A soft Contact Lens Search Coil for Measuring Eye Movements," Vision Research, vol. 25, No. 11, pp. 1629-1633, 1985.

Lupu, R.G. et al., "A Survey of Eye Tracking Methods and Applications," Gheorghe Asachi Technical University of Iasi, Aug. 29, 2013, pp. 71-86.

Paperno et al., A New Method for Magnetic Position and Orientation Tracking, IEEE Transactions on Magnetics, vol. 37, No. 4, Jul. 2001, pp. 1938-1940.

(56) References Cited

OTHER PUBLICATIONS

Umraiya, A, "Design of Miniaturized Coil System Using Mems Technology for Eye Movement Measurement," McGill University, Montreal, Aug. 2009, pp. i-69.

* cited by examiner

HEADGEAR PROVIDING INDUCTIVE COUPLING TO A CONTACT LENS

BACKGROUND

1. Technical Field

This disclosure relates generally to inductive coupling to a coil in a contact lens, for example for the wireless transmission of power.

2. Description of Related Art

Powered contact lenses are contact lenses that contain devices that require a power source to operate. For example, a powered contact lens may include a tiny projector(s) that projects images onto the user's retina. One way that power can be supplied to a contact lens is through inductive coupling. A source coil (also referred to as a transmitter coil) located outside the contact lens produces a time-varying magnetic field, which inductively couples to a corresponding receiver coil in the contact lens. This then provides power to the electrical components in the contact lens. However, given that the size, shape and location of the receiver coil is constrained because it is contained in the contact lens, it can be challenging to efficiently couple power from the transmitter coil to the receiver coil.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which are apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1A:
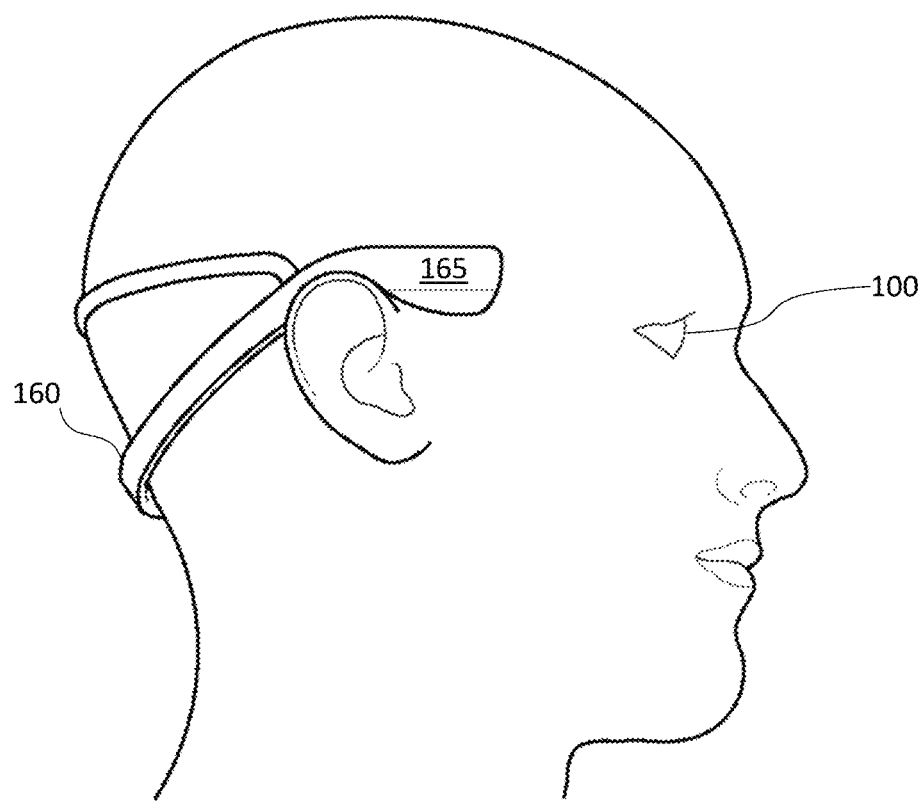
FIG. 1A shows a user operating a contact lens based system that includes a receiver coil in a scleral contact lens and a transmitter coil in a head band accessory.
Figure 1B:
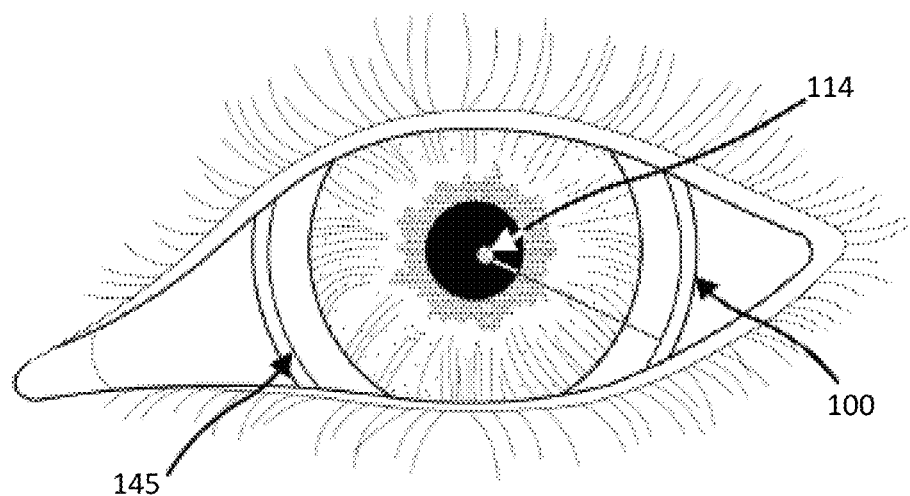
FIG. 1B shows a plan view of the contact lens mounted on the user's eye.
Figure 1C:
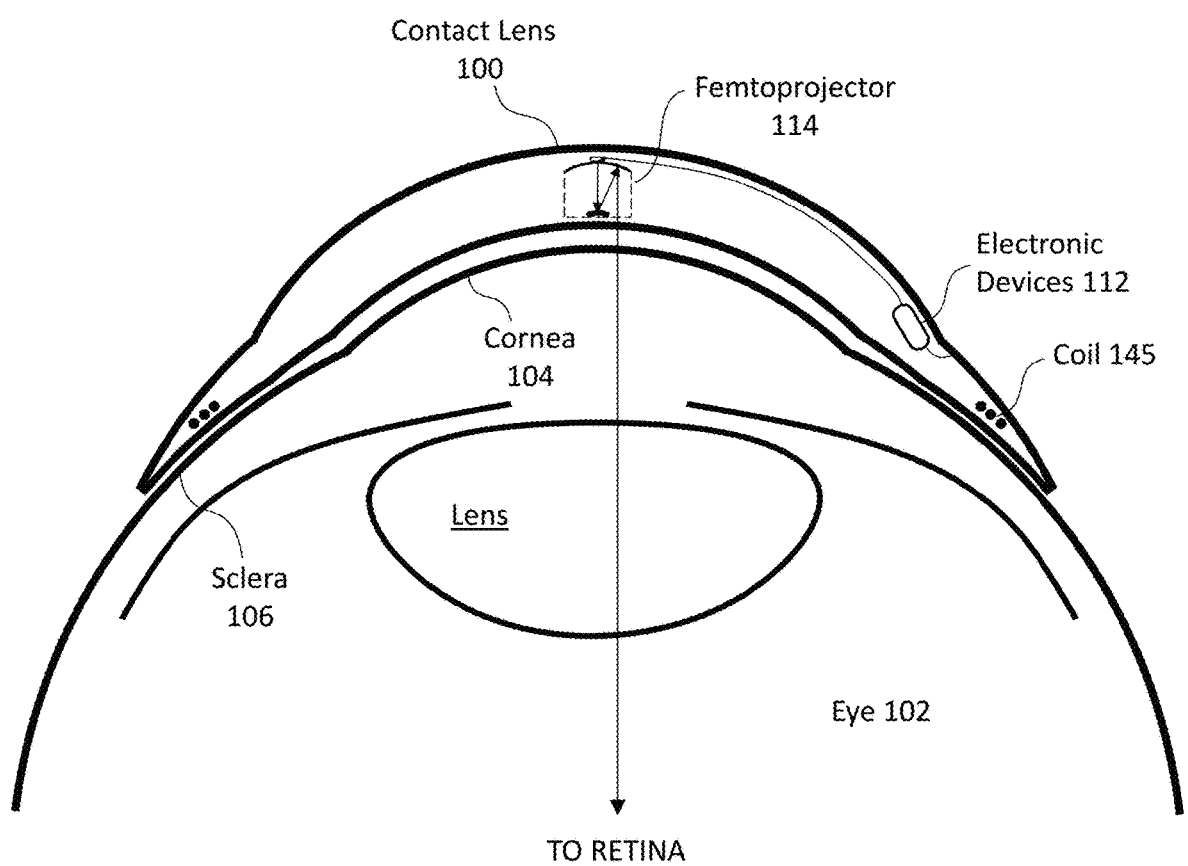
FIG. 1C shows a cross sectional view of the contact lens mounted on the user's eye.

FIG. 1A shows a user operating a contact lens based system that includes a receiver coil in a contact lens 100 and a transmitter coil 165 in a head band accessory 160. The transmitter coil 165 may be embedded within the accessory and not visible from the outside. FIGS. 1B and 1C show a plan view and a cross sectional view of the contact lens 100 with receiver coil 145 mounted on the user's eye. In this system, the transmitter coil 165 wirelessly transfers power to the receiver coil 145 in order to power the electronic components 112, 114 in the contact lens 100.

The efficiency of the inductive coupling depends on the relative positioning of the transmitter and receiver coils 165, 145. The coupling efficiency between the transmitter and receiver coils 165, 145 depends on their alignment (i.e., whether the direction of the magnetic field produced by the transmitter coil is parallel to the axis of the receiver coil), the distance between the coils, and whether the coils are similar in size and shape. The size, shape and location of the receiver coil 145 is constrained, because it is contained in the contact lens 100. Therefore, most of the design freedom lies in the size, shape and location of the transmitter coil 165. Other factors such as orientation of the contact lens 100 and overall aesthetics also affect the design of the transmitter coil 165.

In one approach, the transmitter coil 165 is contained in a headgear 160, which in the example of FIG. 1 is a head band. When the user wears the headgear 160, the transmitter coil 165 is positioned on a side of the user's head and between the user's ear and the user's eye opening. In FIG. 1A, the head band 160 loops from one ear behind the user's head to the other ear, and also extends slightly forward of each ear. The transmitter coil(s) 165 may be located in the portion of the headband 160 that extends forward of each ear or at least forward of the back edge of the ear. This is approximately the location of the temples for a pair of glasses and it is the location closest to the contact lens 100. Typically, this places the front edge of the transmitter coil 165 within 40-50 mm of the user's eye opening, while still maintaining an unobtrusive aesthetic.

Different transmitter coils 165 may be used, as is illustrated by the examples in the figures below. The axis of the transmitter coil 165 may be approximately perpendicular to the coronal plane of the user's head (i.e., aligned to the front-back direction as defined by the user's head). Alternatively, the axis may be orthogonal to this direction (i.e., aligned to the left-right direction). There may also be more than one transmitter coil, and there may be transmitter coil(s) on both the right and left sides of the user's head as well as at other locations. Shielding, ferrite cores, ferrite lids, Litz wire and other components may be used to shape the magnetic field, both to increase coupling to the receiver coil and to reduce undesirable field effects.

If there is more than one transmitter coil, a controller may coordinate the magnetic fields produced by the transmitter coils to achieve a desired result. For example, the controller may control the strength of the magnetic fields produced by the transmitter coils to generate a resultant magnetic field at the receiver coil that has a certain strength and/or orientation. In one approach, the orientation of the contact lens is tracked and this is used as feedback for the controller. The actual power transfer may also be used as feedback for the controller. In another approach, a certain range of eye movement is assumed, and the magnetic fields are controlled so that the resultant magnetic field at the receiver coil provides good average inductive coupling over the assumed range of motion.

Besides (or in addition to) wireless power transfer, the inductive coupling between the coils may be used to determine an orientation of the user's eye, since the coupling efficiency changes with position of the receiver coil. For this task, transmitter coils with different orientations are used, for example three transmitter coils having orthogonal axes. The coupling with each of the different coils may be distinguished based on time division multiplexing, frequency division multiplexing or code division multiplexing. The eye orientation may be used for eye tracking purposes or to increase the efficiency of the wireless power transfer.

Returning to FIG. 1, the powered contact lens 100 in this figure is a scleral contact lens, which is designed to not move around on the user's eye. The eye 102 includes a cornea 104 and a sclera 106. The scleral contact lens 100 is supported by the sclera 106 and vaults over the cornea 104. Oxygen permeates through the contact lens 100 to the cornea 104.

The powered contact lens 100 contains payload(s), including electronics that require a power source. Power is provided by the receiver coil 145. In the example of FIG. 1, the payloads include a small projector that projects images onto the user's retina (referred to as a femtoprojector 114) and the corresponding electronics 112 to operate the femtoprojector. These are powered by the receiver coil 145, which is positioned around the periphery of the contact lens. The femtoprojector 114 may include an LED frontplane with an LED array, an ASIC backplane with electronics that receives the data to drive the LED frontplane, and optics to project light from the LED array onto the retina. The femtoprojector 114 preferably fits into a 2 mm by 2 mm by 2 mm volume or even into a 1 mm by 1 mm by 1 mm volume. The femtoprojector 114 is positioned over the cornea since it projects images onto the retina. The electronics 112 may be positioned away from the cornea, as shown in FIG. 1.

Other examples of powered payloads include sensors, cameras, and eye tracking components such as accelerometers, gyroscopes and magnetometers. Payloads may also include passive devices, such as a coil or antenna for wireless power or data transmission, batteries and capacitors for energy storage, and passive optical structures (e.g., absorbing light baffles, beam-splitters, imaging optics). The contact lens 100 may also contain multiple femtoprojectors, each of which projects images onto the user's retina. The contact lens 100 moves with the user's eye 102 as the eye rotates in its socket. Because the femtoprojectors are mounted in the contact lens 100, they also move with the user's eye. As a result, each femtoprojector is stationary relative to the user's retina and projects its image to the same region of the retina, even as the user's eye moves around. Some femtoprojector(s) may always project images to the fovea, and other femtoprojector(s) may always project images to more peripheral regions which have lower resolutions. As a result, different femtoprojectors may have different resolutions. The images from different femtoprojectors may be overlapping, to form a composite image on the user's retina.

In the example of FIG. 1, the receiver coil 145 is positioned around the periphery of the contact lens. This maximizes the area of the coil 145 but confines the coil to a specific position within the contact lens. The size, shape and location of the transmitter coil(s) 165 are selected to maximize inductive coupling to the receiver coil 145. In addition, the receiver coil 145 may move relative to the transmitter coil 165. Scleral contact lenses are designed so that they do not move with respect to the user's eye. However, the user's eye moves as the user looks to the right and left, or looks up and down. The size, shape and location of the transmitter coil(s) should also account for this eye movement.

Figure 2:
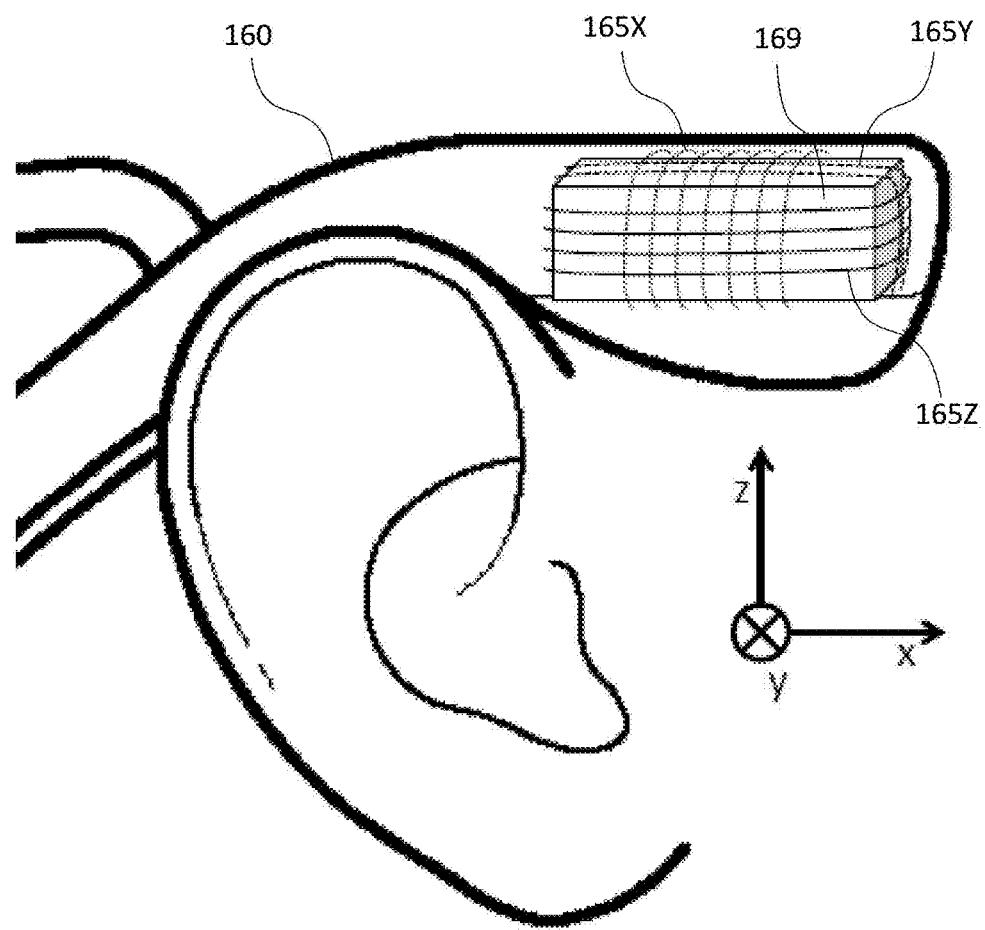
FIG. 2 shows a set of transmitter coils in the head band accessory.

FIG. 2 shows a set of three transmitter coils 165X,Y,Z built into the head band accessory 160. FIG. 2 also shows an x-y-z coordinate system. The x-direction (i.e., parallel to the x-axis) is perpendicular to the coronal plane of the user's head and is also referred to as the front-back direction. The +x direction is the user's forward-looking direction. The y-direction is perpendicular to the sagittal plane of the user's head and is also referred to as the left-right direction. The z-direction is perpendicular to the transverse or axial plane of the user's head.

The transmitter coils 165 have axes that are orthogonal to each other. Transmitter coil 165X has an axis oriented along the x-direction (perpendicular to the coronal plane). Coils with this orientation are referred to as end-firing. Transmitter coil 165Y has an axis oriented along the y-direction (perpendicular to the sagittal plane) and is referred to as side-firing. Transmitter coil 165Z has an axis oriented along the z-direction and is referred to as top-firing. In this example, all three coils 165 enclose a shared core volume 169, which may be air, a non-ferrite material (such as plastic), or a ferrite core.

In FIG. 2, the transmitter coils 165 are positioned forward of the user's ear but behind the user's eye opening. This allows the transmitter coils 165 to be positioned close to the contact lens and receiver coil, while maintaining an unobtrusive aesthetic. To maintain the aesthetic, it may also be desirable for the coils to be thin along the y-direction. In some designs, the set of transmitter coils has a thickness (along the y-direction) of not more than 10 mm, not more than 5 mm, or not more than 2 mm in thinner designs. Reducing the thickness of the design may reduce the strength of the magnetic fields produced. This may be compensated by increasing the driving current, increasing the coil area, increasing the number of coil turns, increasing effective permittivity by using custom shaped ferrite cores and/or reducing the distance between the transmitter and receiver coils.

Given these size constraints, the different coils 165 may have different designs. The end-firing coil 165X is thin due to the thickness constraint, so each individual winding has a relatively small area. As a result, the coil 165X may have many windings in order to generate the desired magnetic field and/or may be wound around a high aspect ratio ferrite core resulting in higher effective permittivity and stronger fields. Conversely, the geometry constraints allow the side-firing coil 165Y to have a relatively large area and fewer windings may be used. In addition, the area for the side-firing coil 165Y may be an unusual shape, an irregular shape or L-shaped for example, in order to make use of the available area.

Figure 3A:
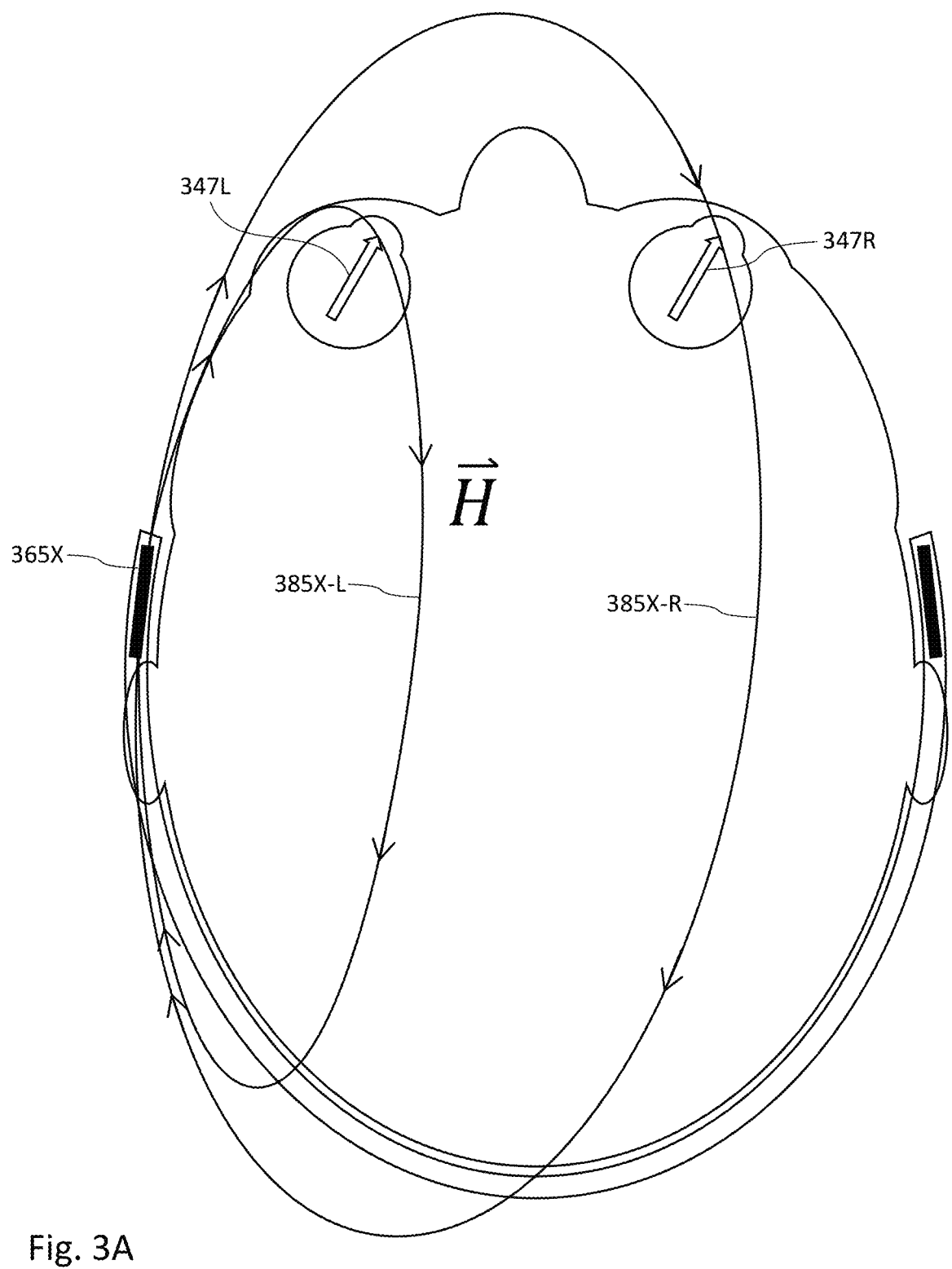
FIGS. 3A and 3B show magnetic field lines produced by transmitter coils of different orientation.
Figure 3B:
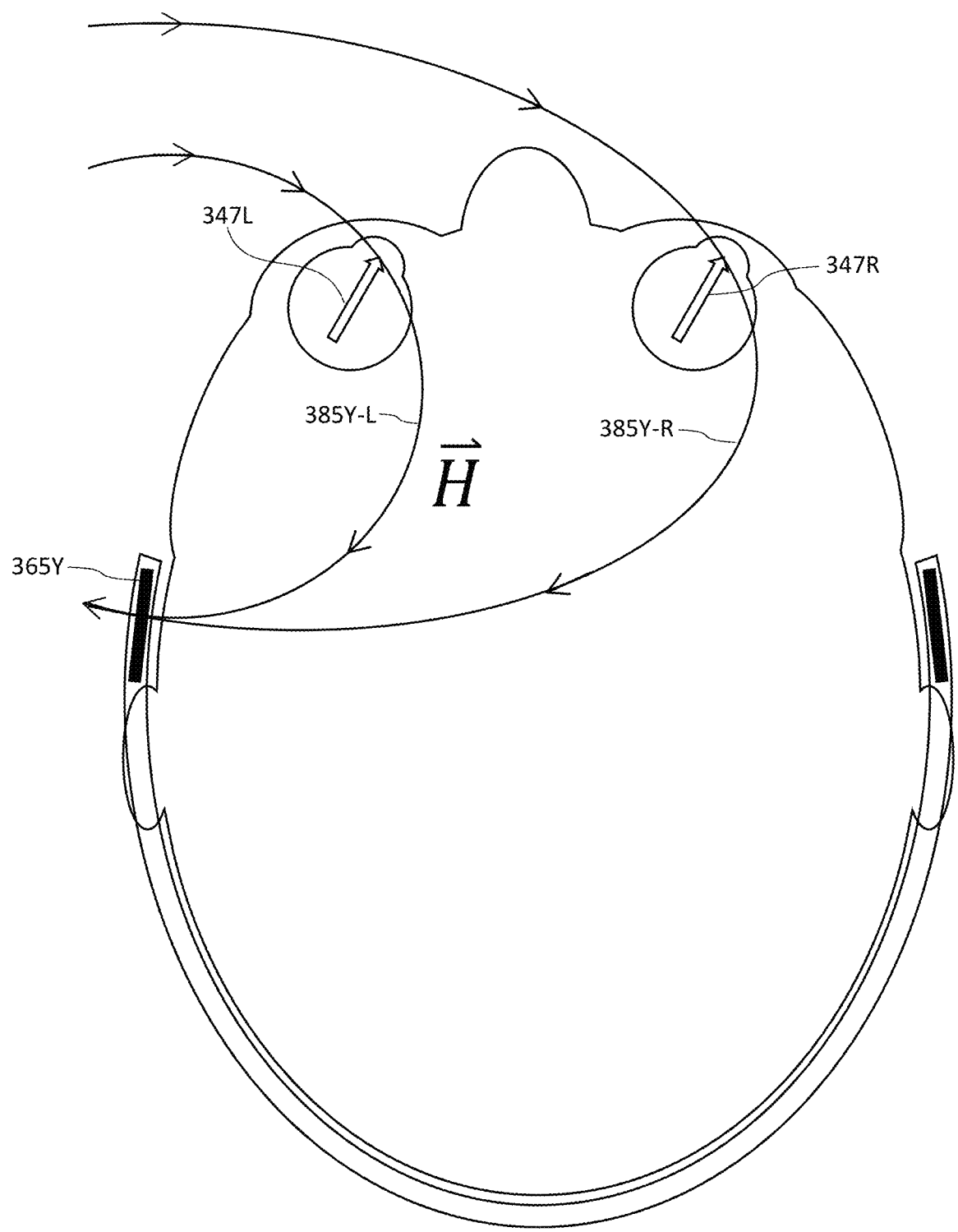

FIGS. 3A and 3B show magnetic field lines produced by an end-firing transmitter coil 365X and a side-firing transmitter coil 365Y, respectively. These figures show a cross sectional view taken through an x-y plane. The transmitter coils 365 and receiver coils are assumed to be located at approximately a same z-height. The receiver coils are not expressly shown, but their orientations are indicated by the arrows 347. The tip of each arrow 347 indicates the center of the receiver coil and the direction of the arrow indicates the orientation of the axis of the receiver coil. A magnetic field line 385 that is aligned with an arrow 347 couples efficiently to that receiver coil. A magnetic field line 385 that is perpendicular to the arrow 347 has low coupling efficiency. In these figures, the user is looking to the right.

FIG. 3A is a conceptual diagram that shows magnetic field lines 385X-L and 385X-R produced by end-firing transmitter coil 365X. Magnetic field line 385X-L goes through the tip of arrow 347L for the left contact lens, and magnetic field line 385X-R goes through the tip of arrow 347R for the right contact lens. Analogously, FIG. 3B shows magnetic field lines 385Y-L and 385Y-R produced by side-firing transmitter coil 365Y. Magnetic field line 385Y-L goes through the tip of arrow 347L for the left contact lens, and magnetic field line 385Y-R goes through the tip of arrow 347R for the right contact lens. The angle between the magnetic field line 385 and orientation arrow 347 indicates the inductive coupling between the transmitter coil and the receiver coil.

The field lines 385 in FIG. 3 are used to illustrate that the coupling between each transmitter coil 365 and each receiver coil varies depending on the orientation of the transmitter coil (end-firing vs side-firing), the location of the transmitter coil (left side of head or right side of head), the location of the receiver coil (left eye or right eye), and the orientation of the receiver coil (user looking left or right). If the direction of the magnetic field line 385 is given by the unit vector $\hat{H}$ and the orientation of arrow 347 (i.e., axis of the receiver coil) is given by the unit vector $\hat{n}$, then the efficiency of the inductive coupling is proportional to the dot product $\hat{H}\cdot\hat{n}$.

Figure 4A:
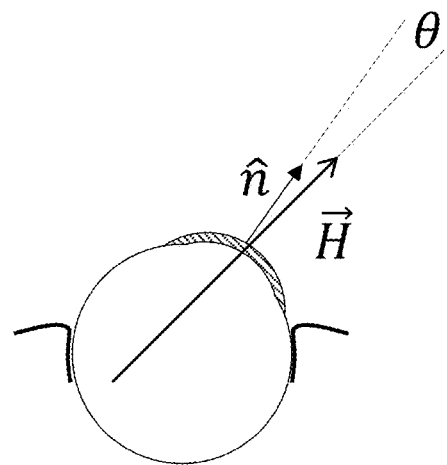
FIGS. 4A-4C shows the change in inductive coupling to a receiver coil in a contact lens, as the eye moves within the eye socket.
Figure 4B:
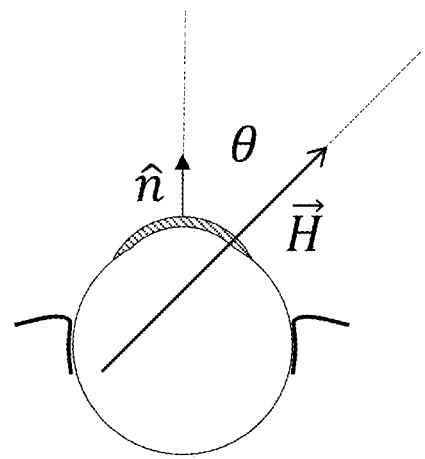
Figure 4C:
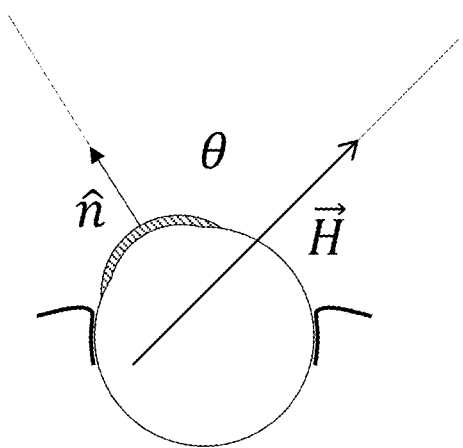

In FIG. 3, the user is looking to the right. FIGS. 4A-4C shows the change in inductive coupling as the eye moves within the eye socket. In FIGS. 4A-4C, the user is looking to the right, looking straight ahead, and looking to the left, respectively. The orientation of the magnetic field $\vec{H}$ is constant in this example. The orientation $\hat{n}$ of the axis of the receiver coil changes as the user looks in different directions, and the angle θ between $\vec{H}$ and $\hat{n}$ also changes. The inductive coupling is proportional to cos (θ) and the power coupling is proportional to $\cos^2(\theta)$.

In addition to the arrangement of the transmitter coil itself, both the direction and the strength of the magnetic field $\vec{H}$ may also be affected by other structures. For example, a ferrite core may be used to improve the performance of the coil. The windings themselves may also take different forms: Litz wire or solid wire for example.

Figure 5A:
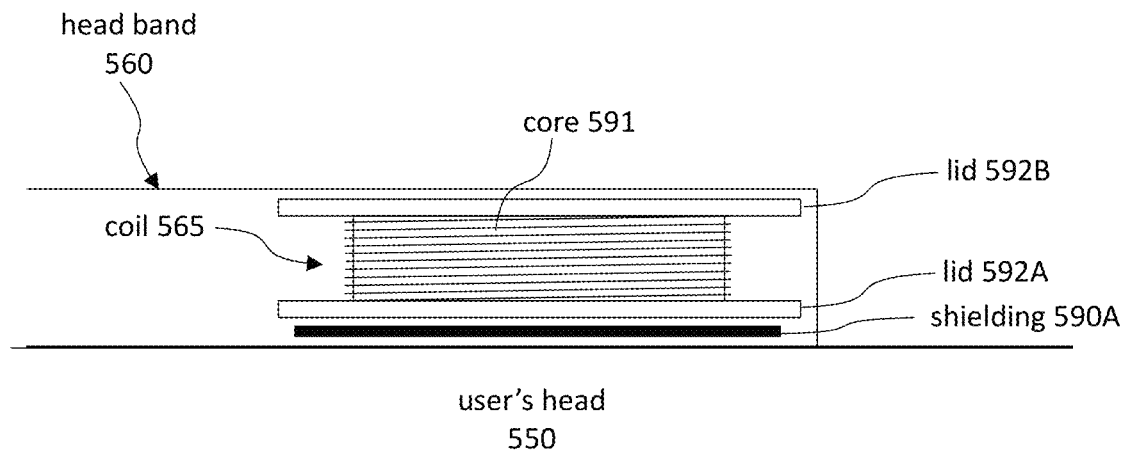
FIGS. 5A and 5B show a transmitter coil with shielding and a ferrite lid.

As another example, FIG. 5A shows a transmitter coil 565 with a ferrite core 591, ferrite lids 592A-B and shielding 590A. The coil 565 is encapsulated in a head band 560. The shielding 590A may be copper shielding. When the head band is worn, the shielding 590A is positioned between the transmitter coil 565 and the side of the user's head 550. It reduces the magnetic field inside the user's body. The ferrite core 591 and lids 592A-B shape the magnetic field lines. Because the lids 592A-B extend beyond the core and coil turns, magnetic field lines will be established between the two lids 592A-B and this will also shape the magnetic field lines at the location of the receiver coils. The ferrite lids 592 extend beyond the copper shielding 590 in order to reduce eddy current losses.

Figure 5B:
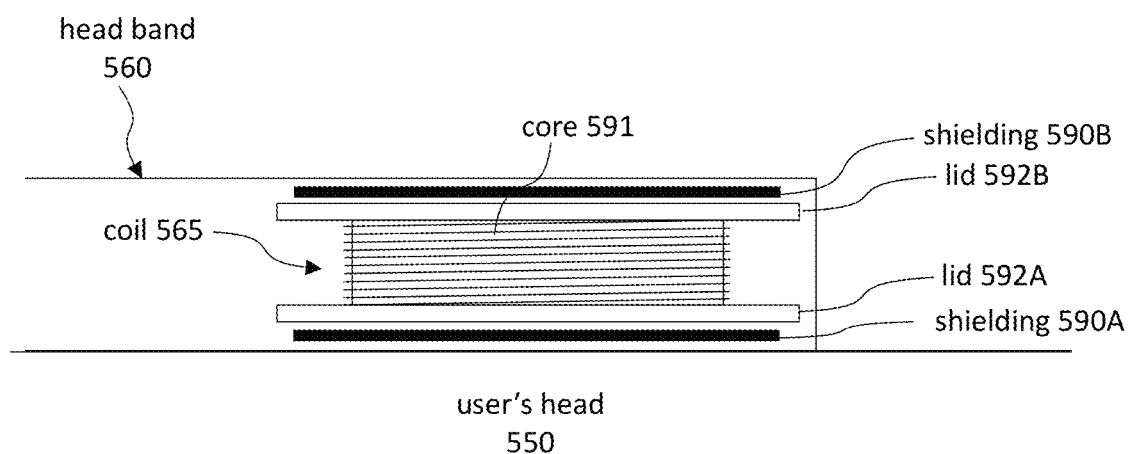

The design of FIG. 5B also includes shielding 590B on the side away from the user's head. This reduces the magnetic field outside the user's head, thus reducing any unwanted effects that may result from this magnetic field.

Figure 6A:
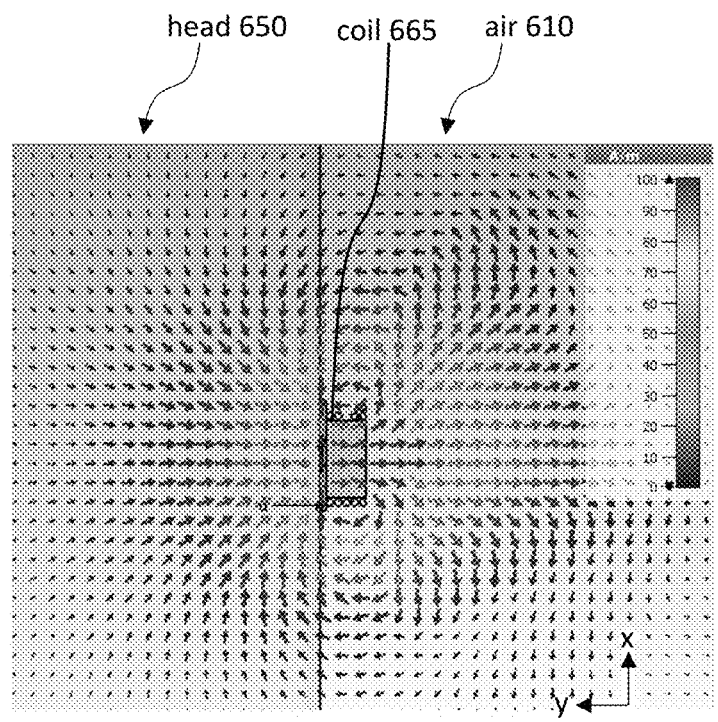
FIGS. 6A and 6B show the field lines for the magnetic field produced by a transmitter coil with and without shielding.
Figure 6B:
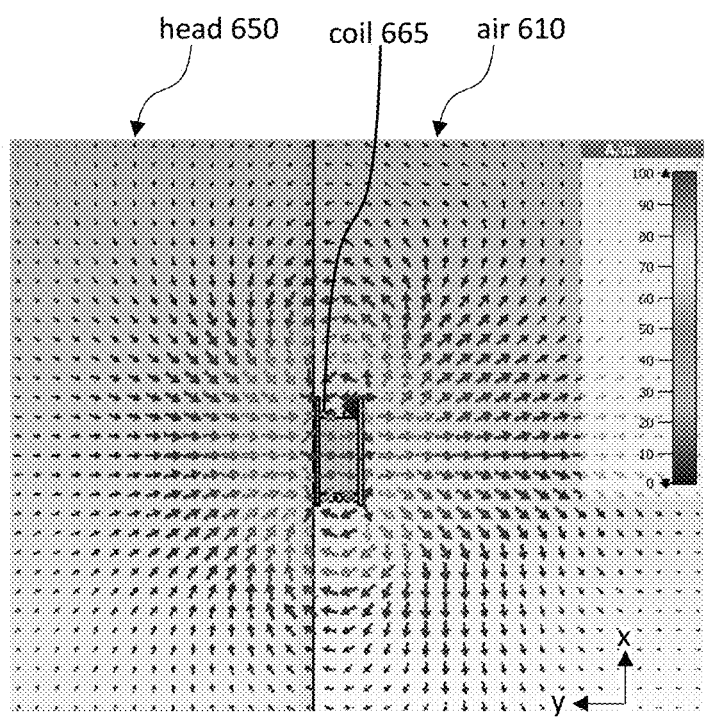

FIGS. 6A and 6B show the magnetic field lines produced by a side-firing transmitter coil with and without the outside shielding, respectively. That is, FIG. 6A corresponds to the coil design of FIG. 5A, and FIG. 6B corresponds to the coil design of FIG. 5B. In both figures, the direction of the magnetic field is shown by the arrows and the strength of the magnetic field is shown by the color of the arrow. Red is strongest and blue is weakest. Within the blue colors, the size of the arrow is an indicator of field strength. The frequency used in this simulation is approximately 13.56 MHz. Alternative frequencies include approximately 6.78 MHz and other unlicensed bands.

The figures show a cross sectional view taken through an x-y plane. The left side of each figure is the user's head 650 and the right side is the external environment 610. The transmitter coil 665 is a side-firing coil on the right side of the user's head. In both figures, the coil 665 has a ferrite core, ferrite lids and copper shielding next to the user's head (elements 591, 592 and 590A in FIG. 5). In FIG. 6B, the coil 665 has additional shielding away from the user's head (element 590B in FIG. 5B), which is not present in FIG. 6A. This reduces the magnetic field immediately to the right of the coil, as shown by the red arrows at that location in FIG. 6A compared to the green arrows in FIG. 6B.

FIGS. 5 and 6 illustrate how the coil assembly affects the magnetic field produced by a transmitter coil. However, the magnetic field produced at any particular point is the vector sum of the magnetic fields produced by each of the individual transmitter coils. In FIG. 3, the resultant magnetic field is the vector sum of the fields produced by the end-firing and side-firing transmitter coils on both the left and right sides of the user's head. In some embodiments, a controller coordinates the individual transmitter coils to produce a desired resultant field at the receiver coil.

Figure 7A:
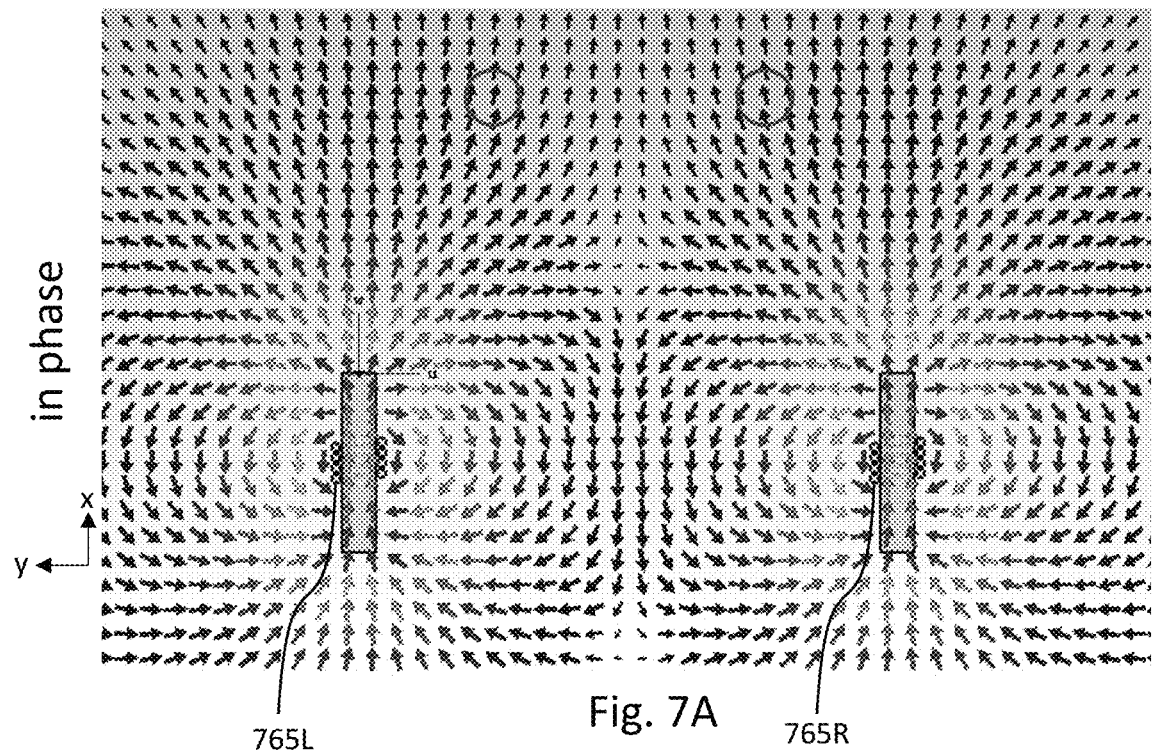
FIGS. 7A and 7B show the field lines for the resultant magnetic field produced by two transmitter coils.
Figure 7B:
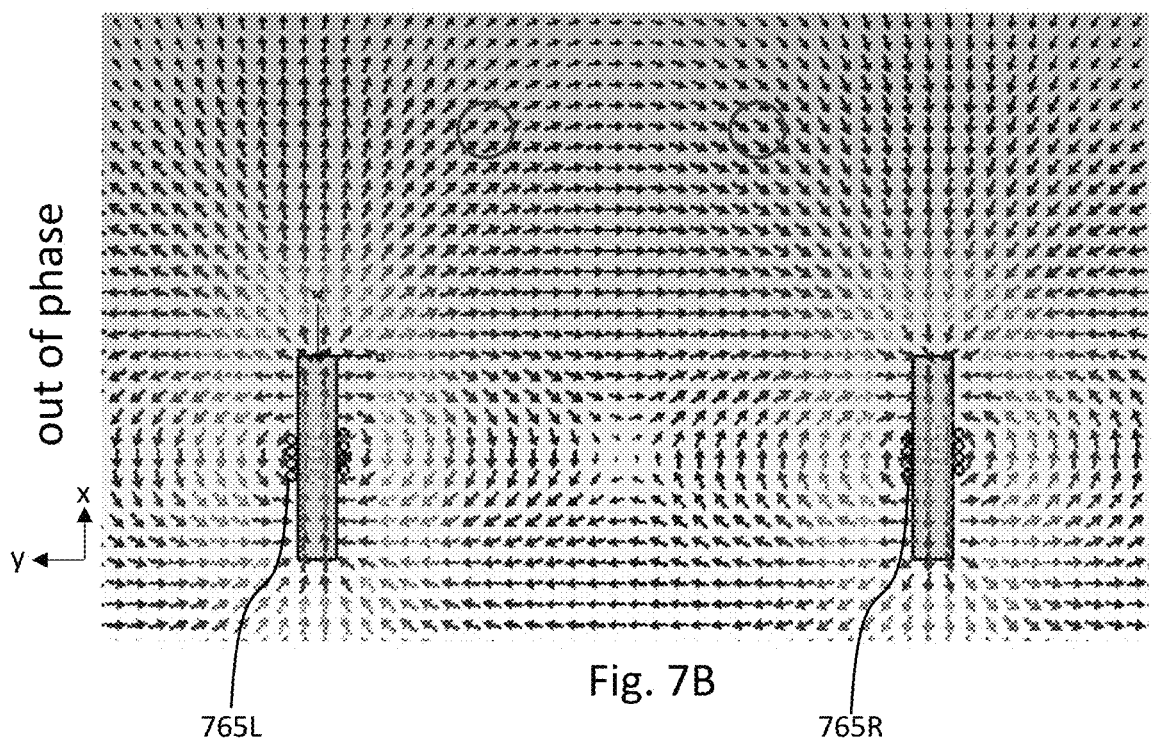

FIGS. 7A and 7B show the field lines for the resultant magnetic field produced by two transmitter coils. The figures show a cross sectional view taken through an x-y plane. In this example, the two coils are both end-firing, with one transmitter coil 765L on the left side of the user's head and one transmitter coil 765R on the right side of the user's head. In FIG. 7A, the two coils 765 are in phase, meaning that the magnetic field within each coil's core is oriented in the same direction. At the time instant shown in FIG. 7A, the field lines are pointing in the +x direction. In FIG. 7B, the two coils 765 are out of phase. The magnetic field within coil 765L's core is pointing in the +x direction, while the magnetic field within coil 765R's core is pointing in the −x direction.

In FIGS. 7A-7B, the red circles represent the approximate locations of the receiver coils for the user's left and right contact lenses. The resultant magnetic field produced at these locations by the two individual transmitter coils is significantly different. In FIG. 7A, the magnetic field lines are oriented predominantly along the x-direction. This produces efficient coupling to both receiver coils when the user is looking straight ahead. In FIG. 7B, the magnetic field lines are oriented at an angle. This produces more efficient coupling to the left receiver coil when the user is looking to the right, and more efficient coupling to the right receiver coil when the user is looking to the left. FIGS. 7A and 7B represent two extremes of in phase and out of phase, other intermediate situations are also possible.

Figure 8:
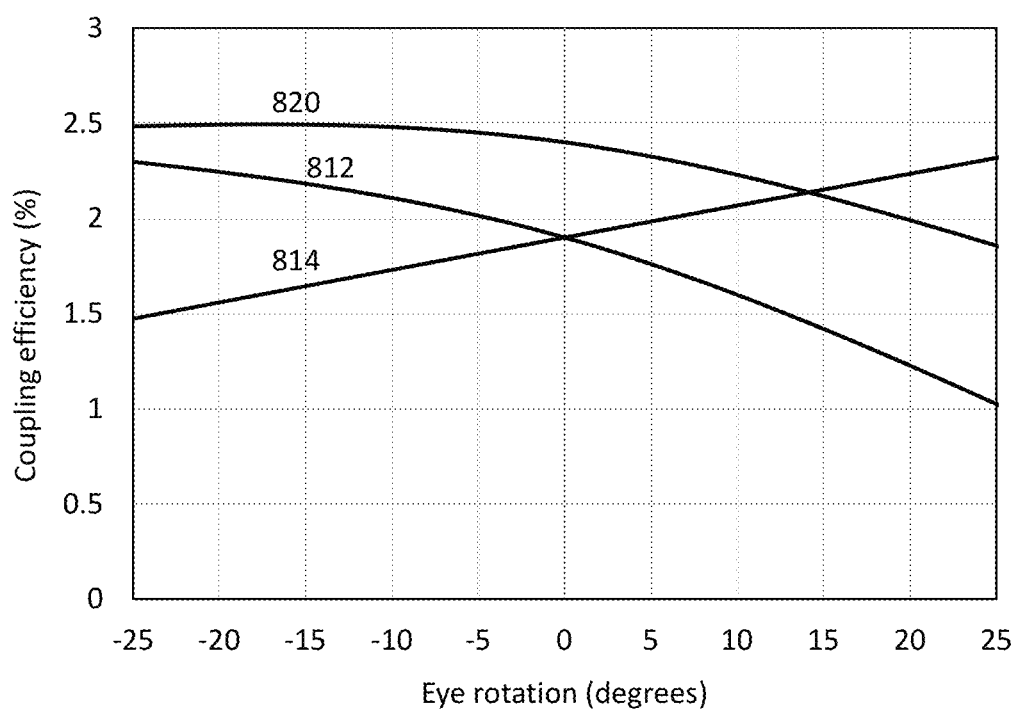
FIG. 8 is a graph of coupling efficiency as a function of eye orientation, for different transmitter coil configurations.

FIG. 8 is a graph of coupling efficiency as a function of eye orientation, for different transmitter coil configurations. Curve 812 shows the efficiency curve for an end-firing transmitter coil coupling to a receiver coil in the near eye contact lens (e.g., right-side end-firing transmitter coil coupling into right-eye contact lens). The x-axis for the graph is the rotation of the eye, looking left and right. The negative degrees are looking in the nasal direction (i.e., right eye looking to the left) and the positive degrees are looking in the temporal direction (i.e., right eye looking to the right). Curve 814 shows the efficiency curve for a side-firing transmitter coil. Curve 820 shows the efficiency curve for a configuration that includes both an end-firing transmitter coil and a side-firing transmitter coil, where approximately equal power is fed into each coil and a controller optimizes the phase shift between the magnetic fields produced by the two coils.

The shape of the magnetic field generated by the side-firing coil may be more uniform across different eye orientations but may have lower peak efficiency. The end-firing coil may have higher peak efficiency but with a steeper drop-off as a function of eye orientation. The steerable configuration 820 has higher average efficiency (i.e., averaged over all eye orientations) than either single-coil configuration. The steerable configuration also has higher efficiency at most eye orientations.

In FIG. 8, the amount of power fed to the end-firing and side-firing transmitter coils is fixed for curve 820. If the controller also varies how much power is fed to each transmitter coil, then the performance is even better. Also note, because of the geometry and placement of the two transmitter coils, their efficiency curves are complimentary. One coil becomes more efficient when the other coil becomes less efficient. For example, at large positive degrees of eye rotation, the efficiency 812 of the end-firing transmitter coil falls dramatically, eventually reaching zero. If equal power is fed to both transmitter coils, this behavior will pull down the overall efficiency. The controller can increase the overall efficiency by feeding more power to the side-firing transmitter and less power (or even zero power) to the end-firing transmitter.

The controller controls the magnetic fields produced by the various transmitter coils to increase the overall power transfer. As mentioned previously, the eye moves and that changes the orientation of the receiver coil(s) relative to the transmitter coil(s). In one approach, eye tracking information is provided to the controller. The magnetic fields produced by the transmitter coils are controlled to optimize the power transfer, given the known orientation of the receiver coil(s). For example, if the user is looking 10 degrees to the right, the controller optimizes power transfer to the receiver coil(s) in that known orientation. The actual power transfer or coupling efficiency may also be used as feedback to the controller. For example, the controller may dither the resultant magnetic field in order to optimize or average out power transfer.

In a different approach, the controller may not know the orientation of the receiver coil(s). Instead, the magnetic fields produced by the transmitter coils are controlled according to a model of the eye motion. For example, if the eye is assumed to rotate between 25 degrees to the left and 25 degrees to the right (or even between +/−35 degrees), the controller may optimize for maximum power transfer assuming some statistical distribution over that range. Alternately, the controller may be based on ensuring that the power transfer never falls below a minimum level for all possible eye orientations. In some cases, the controller may generate a resultant magnetic field at the receiver coil that oscillates in direction as a way to time average over eye orientation.

Control of the magnetic fields also depends on the configuration of transmitter coil(s) and the configuration of receiver coil(s). In some configurations, there may be only one set of transmitter coil(s), which is located either on the right side or on the left side of the user's head. Alternatively, there may be two sets of transmitter coil(s), one on the right side and one on the left side of the user's head. In that case, the left-side and right-side sets of transmitter coils may be the same, may be mirror images of each other or may be different (i.e., asymmetric with respect to left-right symmetry). The left-side and right-side sets of transmitter coils may even have different numbers of coils.

In some cases, the transmitter coils may all have axes that are parallel to the x-y plane (i.e., axial plane), such as end-firing and side-firing coils. Top-firing coils are less useful because they may produce magnetic fields at the receiver coil that are orthogonal to the axis of the receiver coil. In contrast, end-firing and side-firing coils produce magnetic fields at the receiver coil that lie in the x-y plane. Since the axis of the receiver coil rotates in the x-y plane as the user looks left and right, the controller can coordinate the contributions from the end-firing and side-firing coils to produce a resultant magnetic field that is better aligned to the axis of the receiver coil.

The number of receiver coils may also affect the controller function. If there are two receiver coils, one each for left and right contact lenses, the controller considers power transfer to both receiver coils. It may be that maximum power transfer to one contact lens may result in unacceptably low power transfer to the other contact lens. Some tradeoff may be required.

In addition to power transfer, the coupling between transmitter and receiver coils may also be used to track the orientation of the receiver coil. The orientation of the eye affects the inductive coupling between coils. Conversely, if the inductive coupling between coils is known, then the orientation of the eye may be determined. In one configuration, three transmitter coils with orthogonal axes are all located on one side of the user's head, for example a set that includes an end-firing, side-firing and top-firing transmitter coil. Alternatively, the three transmitter coils may have axes that are not orthogonal, as long as they are not all coplanar in orientation. In a different configuration, two sets are used, one on the left side and one on the right side. Each set has two or three transmitters with orthogonal axes, for example an end-firing and a side-firing transmitter coil.

The coupling between different transmitter coils and the receiver coil may be identified by using multiplexing techniques, such as time division multiplexing, frequency division multiplexing or code division multiplexing of the magnetic fields produced by the transmitter coils. The coupling may also be determined in the reverse direction, where the coil in the contact lens transfers power to each of the other coils.

Figure 9:
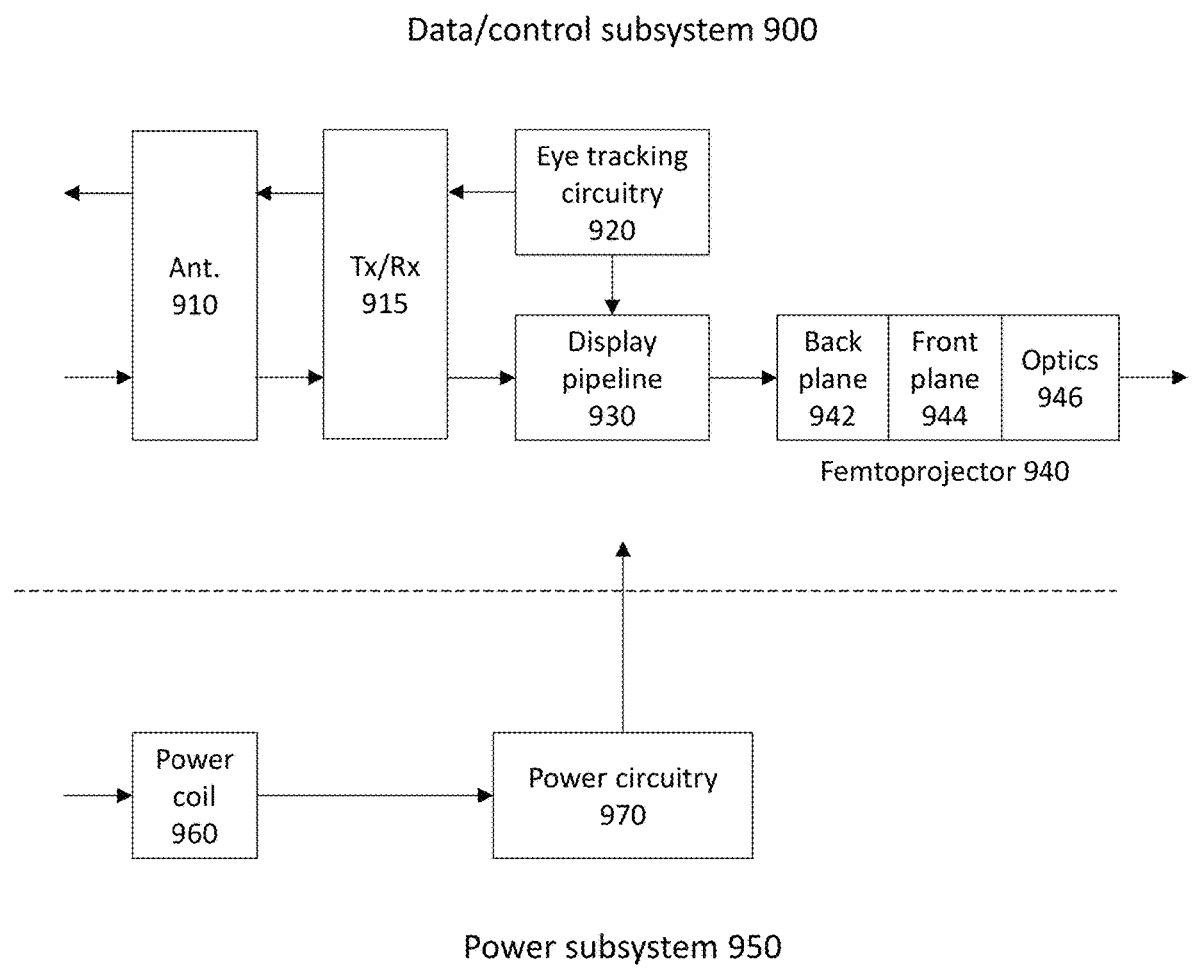
FIG. 9 is a functional block diagram of an eye-mounted display using a scleral contact lens.

FIG. 9 is a functional block diagram of an eye-mounted display using the contact lens system described above. The display can be divided into a data/control subsystem 900 and a power subsystem 950.

In this example, the receive path of the data/control subsystem 900 includes an antenna 910, receiver circuitry 915, a data pipeline 930, and a femtoprojector 940. Data from an external source is wirelessly transmitted to the display via the antenna 910. The receiver circuitry 915 performs the functions for receiving the data, for example demodulation, noise filtering, and amplification. It also converts the received signals to digital form. The pipeline 930 processes the digital signals for the femtoprojector 940. These functions may include decoding, and timing. The processing may also depend on other signals generated internally within the contact lens, for example eye tracking 920 or ambient light sensing. The femtoprojector 940 then projects the corresponding images onto the wearer's retina.

In this example, the femtoprojector 940 includes a CMOS ASIC backplane 942, LED frontplane 944 and optics 946.

The data/control subsystem 900 may also include a back channel through transmitter circuitry 915 and antenna 910. For example, the contact lens may transmit eye tracking data, control data and/or data about the status of the contact lens.

Power is received wirelessly on the contact lens via a power receiver coil 960, which is inductively coupled to power transmitter coil(s) as described above. This is coupled to circuitry 970 that conditions and distributes the incoming power (e.g., converting from AC to DC if needed). The power subsystem 950 may also include energy storage devices, such as batteries or capacitors.

In addition to the components shown in FIG. 9, the overall system may also include components that are outside the contact lens (i.e., off-lens). For example, head tracking and eye tracking functions may be performed partly or entirely off-lens. The data pipeline may also be performed partially or entirely off-lens. Each of the arrows on the lefthand side of FIG. 9 also connects to an off-lens component. The power transmitter coil is off-lens, the source of image data and control data for the contact lens display is off-lens, and the receive side of the back channel is off-lens.

There are many ways to implement the different system functions. Some portions of the system may be entirely external to the user, while other portions may be incorporated into the headgear described above. In addition to the transmitter coil(s), the headgear may contain a battery or other power source; eye tracking or head tracking components such as accelerometers, gyroscopes, and magnetometers; components for the data/control path; and radios and antennae and other wireless communication components. Various system components may also be worn on a belt, armband, wrist piece, necklace, or other types of packs.

Although the detailed description contains many specifics, these should not be construed as limiting the scope of the invention but merely as illustrating different examples. It should be appreciated that the scope of the disclosure includes other embodiments not discussed in detail above. For example, other types of headgear may be used. One example is head phones where the transmitter coil is incorporated into the head phone, for example encircling the ear. Another example is hats or helmets, with the transmitter coils built into the hat/helmet or provided as part of an insert to the hat/helmet. Another example is glasses or goggles, where the transmitter coil may be contained in the temple.

Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

Alternate embodiments of some components are implemented in computer hardware, firmware, software, and/or combinations thereof. Implementations can be implemented in a computer program product tangibly embodied in a machine-readable storage device for execution by a programmable processor; and method steps can be performed by a programmable processor executing a program of instructions to perform functions by operating on input data and generating output. Embodiments can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor receives instructions and data from a read-only memory and/or a random-access memory. Generally, a computer includes one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

What is claimed is:

1. A system for providing power to one or more electronic components of an eye-mounted contact lens worn by a user, comprising:
    a headgear configured to be worn on a head of the user; and
    a set of two or more transmitter coils mounted on the headgear and comprising conductive wire, the two or more transmitter coils each wound around a shared core volume, and configured to inductively couple to at least one receiver coil contained in the contact lens when the contact lens is worn on an eye of the user,
    wherein, when the headgear is worn by the user, the set of transmitter coils is positioned on a side of the user's head and forward of a back edge of the user's ear but behind the user's eye opening.

2. The system of claim 1 wherein the headgear comprises a head band that extends from one of the user's ears behind the user's head to the other of the user's ears, and the set of transmitter coils is contained in the head band.

3. The system of claim 1 wherein the head gear comprises head phones, and the set of transmitter coils is contained in one of the head phones.

4. The system of claim 1 wherein the head gear comprises a hat or helmet.

5. The system of claim 1 wherein the head gear comprises glasses or goggles, and the set of transmitter coils is contained in a temple of the glasses or goggles.

6. The system of claim 1 wherein the set of transmitter coils is positioned between the user's ear and the user's eye opening when the headgear is worn by the user.

7. The system of claim 1 wherein a front edge of the set of transmitter coils is positioned within 40 mm of the user's eye opening when the headgear is worn by the user.

8. The system of claim 1 wherein a first transmitter coil of the set of transmitter coils has a central axis that is perpendicular to a coronal plane of the user's head.

9. The system of claim 1 wherein a second transmitter coil of the set of transmitter coils has a central axis that is perpendicular to a sagittal plane of the user's head.

10. The system of claim 1 further comprising:
    shielding positioned between the set of transmitter coils and the side of the user's head.

11. The system of claim 1 further comprising:
a ferrite lid, wherein the set of transmitter coils is positioned between the ferrite lid and the side of the user's head.

12. The system of claim 1 further comprising:
a pair of ferrite lids located above and below the set of transmitter coils.

13. The system of claim 1 wherein a transmitter coil of the set of transmitter coils is constructed from Litz wire.

14. The system of claim 1 wherein current through a transmitter coil of the set of transmitter coils produces a time-varying magnetic field having a frequency between 13 and 14 MHz.

15. The system of claim 1 wherein the headgear further contains a battery that provides power to drive the set of transmitter coils.

16. The system of claim 1 wherein the headgear further contains a speaker.

17. The system of claim 1 wherein the set of transmitter coils has a thickness of not more than 10 mm.

18. The system of claim 1 wherein the transmitter coils have a shared ferrite core.

\* \* \* \* \*